United States Patent
Coburn

[11] Patent Number: 6,036,577
[45] Date of Patent: Mar. 14, 2000

[54] DISPOSABLE BREAST PAD

[76] Inventor: Shonda L. Coburn, 1020 11th St., Marysville, Calif. 95901

[21] Appl. No.: 09/025,296

[22] Filed: Feb. 18, 1998

[51] Int. Cl.⁷ .................................................. A41C 3/06
[52] U.S. Cl. ............................................................ 450/57
[58] Field of Search .................................. 450/39, 51, 54, 450/55, 57, 68, 81, 93

[56] References Cited

U.S. PATENT DOCUMENTS

| | | |
|---|---|---|
| 2,380,199 | 7/1945 | Stein .......................................... 450/68 |
| 3,442,268 | 5/1969 | Bird . |
| 4,047,534 | 9/1977 | Thomaschefsky et al. . |
| 4,074,721 | 2/1978 | Smits et al. . |
| 4,125,114 | 11/1978 | Repke . |
| 4,333,471 | 6/1982 | Nakai . |
| 4,667,666 | 5/1987 | Fryslie . |
| 4,700,699 | 10/1987 | Tollerud et al. . |
| 4,875,492 | 10/1989 | Mitchell et al. . |
| 4,992,074 | 2/1991 | Diaz . |
| 5,017,174 | 5/1991 | Gowrylow ................................ 450/57 |
| 5,326,305 | 7/1994 | Fochler . |
| 5,447,462 | 9/1995 | Smith et al. ............................... 450/39 |
| 5,603,653 | 2/1997 | Hartman . |

FOREIGN PATENT DOCUMENTS

| | | |
|---|---|---|
| 958747 | 3/1950 | France . |
| 269399 | 4/1927 | United Kingdom . |
| 508399 | 6/1939 | United Kingdom ..................... 450/81 |
| 1143146 | 2/1969 | United Kingdom . |

*Primary Examiner*—John J. Calvert
*Assistant Examiner*—Alissa L. Hoey
*Attorney, Agent, or Firm*—Richard C. Litman

[57] ABSTRACT

A disposable breast pad, which does not require the use of a brassiere for support, comprises a circular body having a surface profile adapted to conform to the contour of the female breast. A portion of the circular body is cut out and removed to form an opening in the circular body. An insert is provided to cover the opening and is attached to the circular body. The insert is made of mesh material and has elastic strands sewn therein. The insert will allow the pad to expand, if necessary, thereby ensuring a comfortable fit for breasts of different sizes and shapes. A pressure sensitive skin safe adhesive is used to secure the pad directly to the breast.

6 Claims, 3 Drawing Sheets

DISPOSABLE BREAST PAD

BACKGROUND OF THE INVENTION

1. Field of the Invention

The present invention relates to absorbent materials worn in contact with the skin, and more specifically, to nursing or breast pads which may be comfortably secured and fitted to breasts of various sizes and shapes without the use of a brassiere.

2. Description of the Related Art

Disposable nursing or breast pads are known in the art and are used by new mothers to prevent milk, which may leak from the breasts, from staining garments worn by the mother. Prior art breast pads require that a brassiere is worn to prevent the pad from slipping out of the proper position. While the use of a brassiere may be desirable for daytime wear, the brassiere may prove to be restrictive and uncomfortable when sleeping. Furthermore, movement during sleep may cause the pad to slip from a proper position thereby causing leaked milk to stain bedding and/or night clothes. Also, the breast pads of the prior art do not adequately adjust to breasts of different sizes and shapes.

U.S. Pat. Nos. 3,442,268 (Bird), 4,047,534 (Thomaschefsky et al.), 4,074,721 (Smits et al.), 4,125,114 (Repke), and French Patent 958,747 show breast pads designed to be inserted into a brassiere.

U.S. Pat. No. 4,667,666 (Fryslie) shows a bandage using a skin safe adhesive.

U.S. Pat. No. 4,992,074 (Diaz) shows a self supporting brassiere with a separate adhesive strip for holding the brassiere in place.

U.S. Pat. Nos. 4,700,699 (Tollerud et al.) and 5,603,653 (Hartman) show breast pads with adhesive on an outer surface so that the pads adhere to a brassiere.

U.S. Pat. No. 5,326,305 (Fochler) shows a breast pad attached to a garment.

U.S. Pat. No. 4,875,492 (Mitchell et al.) shows a breast pad which is molded to fit the breast and supported in a brassiere.

U.S. Pat. No. 4,333,471 (Nakai) shows a breast nipple cover with adhesive for direct attachment to the wearer's skin. The cover is also provided with cut out portions to prevent wrinkles. The cover is constructed of air permeable paper and soft felt and would not be effective to absorb mother's milk.

British Patents Numbers 269,399 and 1,143,146 respectively show padding for garments and a method for making seamless pads.

None of the above inventions and patents, taken either singularly or in combination, is seen to describe the instant invention as claimed. Thus a disposable breast pad solving the aforementioned problems is desired.

SUMMARY OF THE INVENTION

The present invention describes a disposable breast pad which will prevent leakage of mother's milk. The breast pad is an enlarged circular body and is adapted to cover the breast's nipple. The breast pad is constructed of highly absorbent material and has a skin safe adhesive applied around the circumference thereof. The adhesive allows the pad to be secured directly to the breast and to remain in place without the use of a brassiere. A sector shaped portion is cut out of the pad which allows the pad to adjust to breasts of different sizes and shapes while ensuring that the pad completely covers the nipple.

Accordingly, it is a principal object of the invention to provide an improved breast pad which is economical and is easy to use.

It is another object of the invention to provide an improved breast pad that is disposable and especially adapted for nighttime wear.

It is a further object of the invention to provide an improved breast pad that is comfortable and does not require the use of a brassiere.

Still another object of the invention is to provide an improved breast pad that is self adjusting to fit breasts of different sizes and shapes.

It is an object of the invention to provide improved elements and arrangements thereof for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENT

Figure 4:
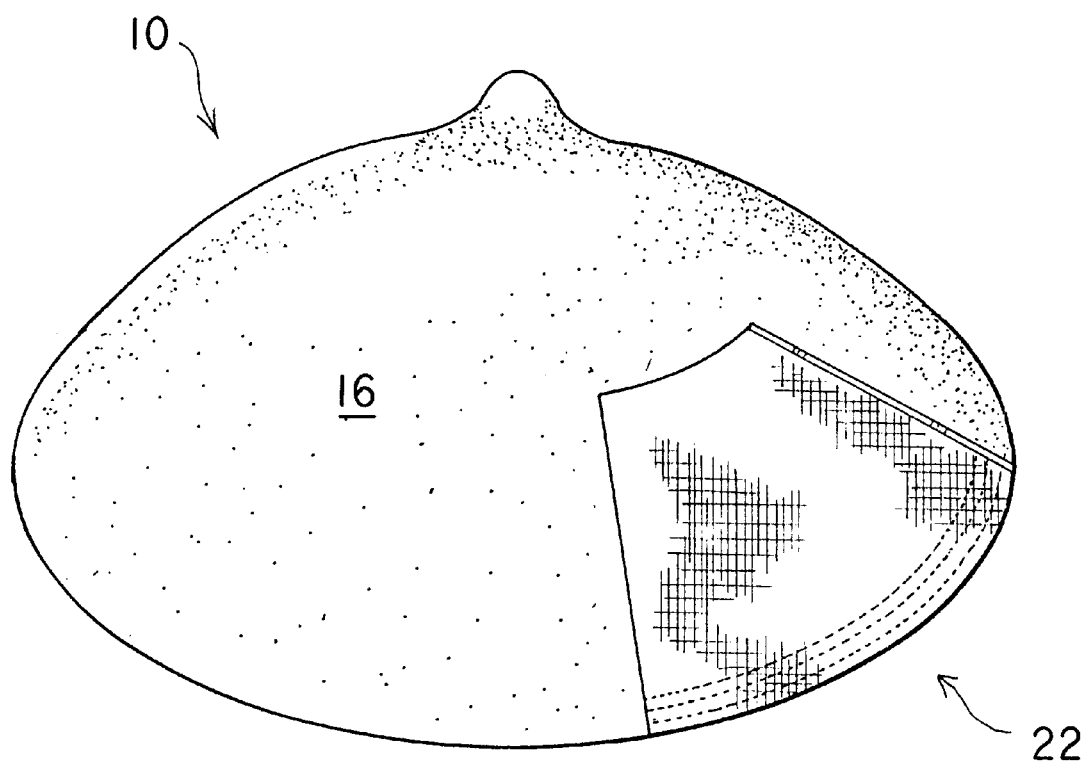
FIG. 4 is a perspective environmental view of a breast pad according to the present invention.

The present invention is a disposable breast or nursing pad constructed as a circular body 10 which has a diametrical dimension of approximately 12 centimeters and wherein the circular body's surface, in profile, is adapted to conform with the contour of the female breast (FIG. 4).

Figure 3:
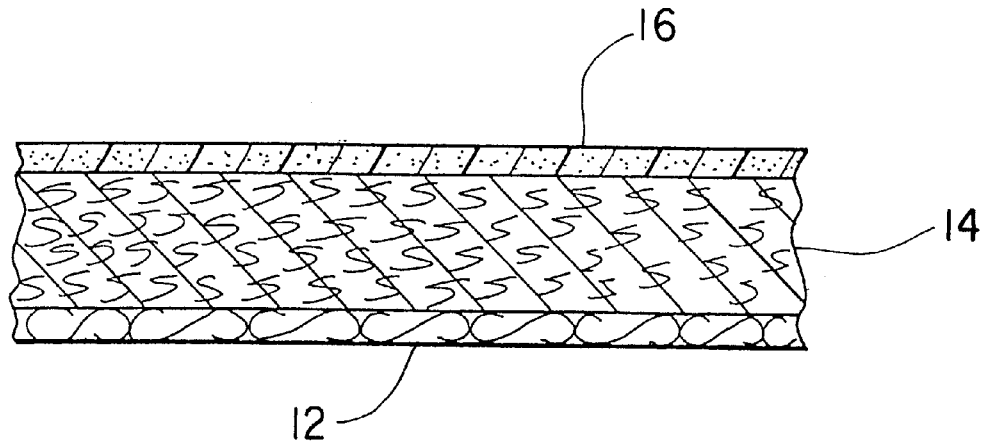
FIG. 3 is a cross-sectional view of a breast pad according to the present invention taken to show the pad's layer construction.

As shown in FIG. 3, the body 10 is constructed of a plurality of coextensive layers. An inner layer 12, which would contact the breast, is moisture permeable and allows fluid to pass therethrough into an absorbent layer 14. An outer layer 16 is impermeable to moisture and prevents passage of fluid thereby preventing staining and/or wetting of any clothing in contact with the outer layer. Layers 12, 14, and 16 may be fabricated from a variety of materials all well known in the art. Such materials are not part of the present inventive concept.

Figure 1:
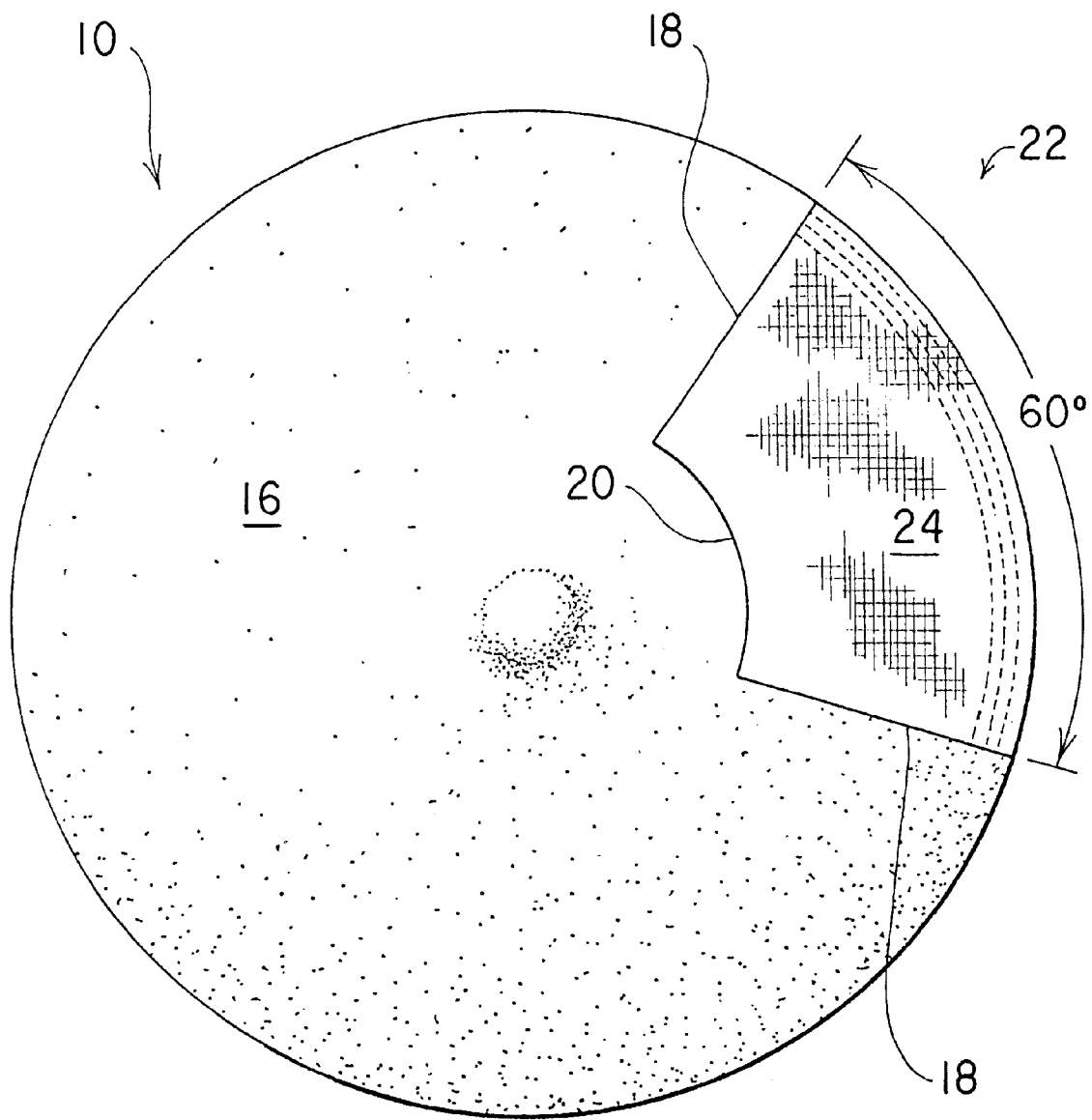
FIG. 1 is a front view of a disposable breast pad according to the present invention.
Figure 2:
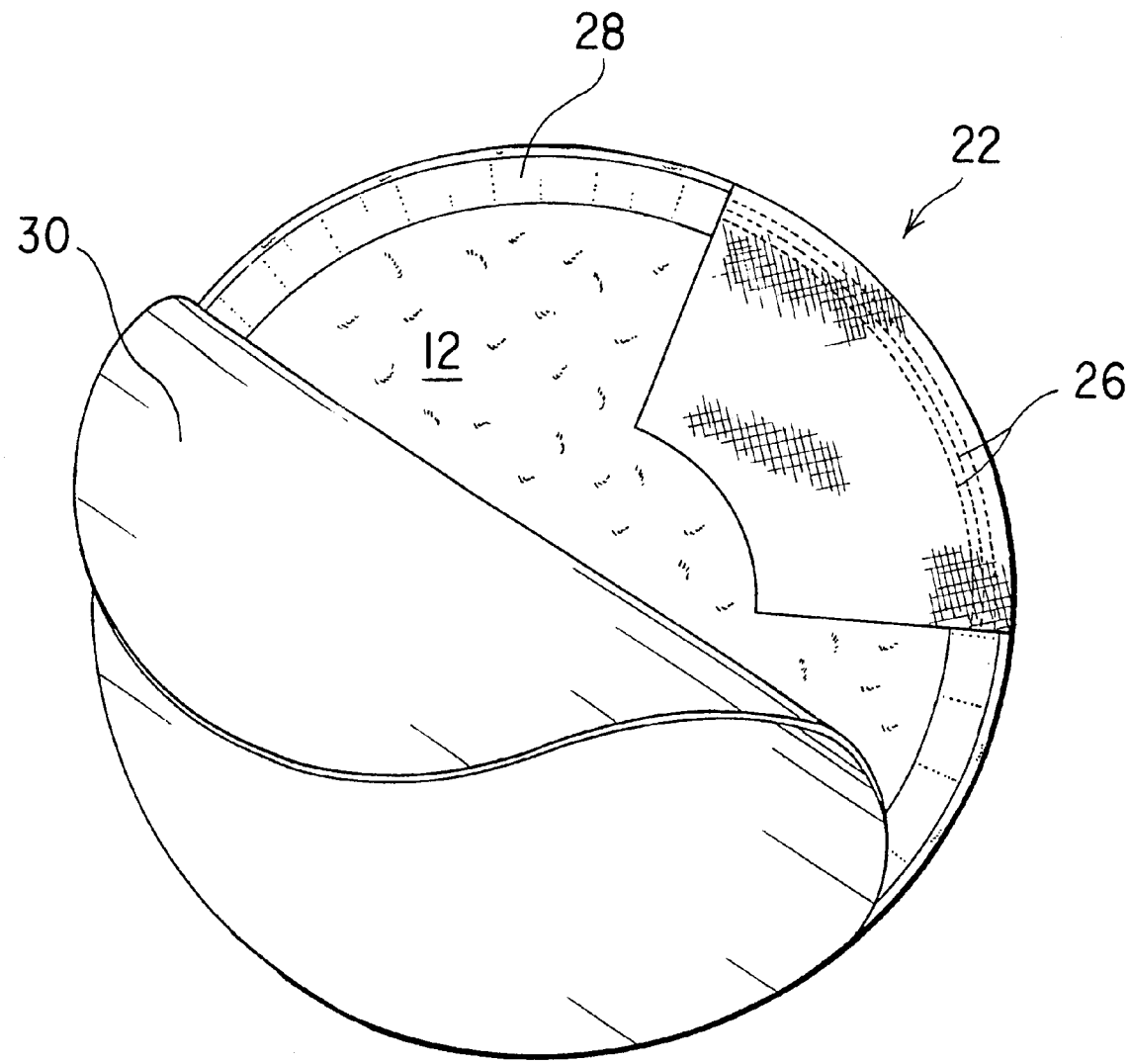
FIG. 2 is a rear view of a disposable breast pad according to the present invention with portions pulled away to show the adhesive bead.

Turning to FIGS. 1 and 2, a portion of the circular body 10 is cut out to form an opening which, in plan view, approximates the configuration of a truncated sector having two sides 18 and a top 20. The sides 18 form an angle of approximately 60 degrees therebetween and extend an equal length of about 4 centimeters from the top 20 to the circumference of the circular body. The truncated apex of the cut out sector leaves a more rounded pad in the center of the circular body such that the pad will completely cover the wearer's nipple.

An insert 22, having substantially the same dimensions as the truncated sector portion cut out of the body 10, is positioned to cover the cut out portion. The insert 22 is constructed of two layers of an air permeable breathable mesh material 24. Materials such as cotton, nylon, rayon, or the like, could be utilized to fabricate the insert. Three strands of elastic 26 (shown in dashed lines) are sewn between the layers of mesh material along a peripheral edge as illustrated in FIGS. 1 and 2. This construction prevents direct contact of the elastic strands with the breast and enhances wearer comfort. The mesh material 24 and elastic strands 26 are securely attached to the body 10 by stitching.

A bead of skin safe pressure sensitive adhesive 28 is applied around the circumference of the circular body on the inner layer thereof such that the adhesive would contact the breast when the pad is worn (FIG. 2). A bead width of approximately 8/10 of a centimeter has been found sufficient to hold the pad in place on the breast. The adhesive does not extend into the area covered by the insert 22. Any of numerous medical pressure sensitive adhesives used on bandages and approved by the U.S. Food and Drug Administration may be employed as an adhesive on the present invention.

A paper backing or release liner 30, shown partly pulled away in FIG. 2, is coextensive with the circumference of the circular body 10. The release liner 30 provides a protective barrier for the adhesive and ensures hygienic conditions for the breast contacting inner layer of the pad.

The invention, as described above, is used by first peeling the paper backing from the circular body 10. The body is then positioned on the breast so that the center of the pad covers the nipple. Gently pressing the pad on the breast will cause the insert 22 to expand, if necessary, thereby ensuring a comfortable fit for any breast size or shape. The pad is then pressed down around the circumference thereof so that the pressure sensitive adhesive will secure the pad to the breast of the user. No brassiere is required to further secure the pad. To remove, the pad is simply peeled from the breast and properly discarded.

It is to be understood that the present invention is not limited to the embodiment described above, but encompasses any and all embodiments within the scope of the following claims.

I claim:

1. A disposable breast pad comprising:
    a circular body, said circular body having a first layer adapted to contact a female breast, said first layer made of moisture permeable material;
    a second layer positioned on said first layer and coextensive therewith, said second layer made of moisture absorbent material;
    a third layer positioned on said second layer and coextensive therewith, said third layer made of moisture impermeable material;
    a portion cut out of said circular body and removed therefrom so as to form an opening in said circular body;
    an insert positioned to cover said opening in said circular body, said insert made of mesh material and comprising separate inner and outer layers;
    adhesive means affixed on said first layer around only a circumferential area of said circular body.

2. A disposable breast pad as defined in claim 1 wherein a release liner, coextensive with said circular body, is positioned to cover said first layer and said adhesive means.

3. A disposable breast pad as defined in claim 1 wherein elastic strands are attached between said mesh inner layer and said mesh outer layer and wherein said elastic strands and said mesh material are attached to said circular body.

4. A disposable breast pad as defined in claim 1 wherein said opening, in plan view, approximates a configuration of a truncated sector having two sides.

5. A disposable breast pad as defined in claim 4 wherein said two sides form an angle of approximately 60 degrees therebetween.

6. A disposable breast pad as defined in claim 4 wherein said two sides are of equal lengths.

* * * * *